(12) United States Patent
Rubin et al.

(10) Patent No.: US 7,033,616 B2
(45) Date of Patent: Apr. 25, 2006

(54) EXTRACTS, COMPOUNDS AND PHARMACEUTICAL COMPOSITIONS HAVING ANTI-DIABETIC ACTIVITY AND THEIR USE

(75) Inventors: Ian Duncan Rubin, Nottingham (GB); Jasjit Singh Bindra, Groton, CT (US); Michael Anthony Cawthorne, Milton Keynes (GB)

(73) Assignee: Phytopharm PLC, Godmanchester (GB)

( * ) Notice: Subject to any disclaimer, the term of this patent is extended or adjusted under 35 U.S.C. 154(b) by 233 days.

(21) Appl. No.: 09/891,615

(22) Filed: Jun. 27, 2001

(65) Prior Publication Data

US 2002/0146468 A1    Oct. 10, 2002

(30) Foreign Application Priority Data

Jun. 30, 2000  (GB) .................................... 0016213

(51) Int. Cl.
 *A61K 35/78*     (2006.01)
 *C07J 5/00*      (2006.01)

(52) U.S. Cl. ........................... 424/725; 514/866; 536/5
(58) Field of Classification Search ................ 424/725; 514/54, 866; 536/123.1, 5
See application file for complete search history.

(56) References Cited

U.S. PATENT DOCUMENTS

| | | | |
|---|---|---|---|
| 4,062,950 A | 12/1977 | Frommer et al. |
| 4,199 A | 1/1978 | Cobia et al. |
| 4,130,714 A | 12/1978 | Sarges |
| 4,174,439 A | 11/1979 | Rauenbusch et al. |
| 4,185,116 A | 1/1980 | Barnish et al. |
| 4,251,528 A | 2/1981 | Brittain et al. |
| 4,254,256 A | 3/1981 | Otani et al. |
| 4,302,447 A | 11/1981 | Horrobin |
| 4,302,477 A | 11/1981 | Mendy et al. |
| 4,393,049 A | 7/1983 | Horrobin |
| 4,436,745 A | 3/1984 | York, Jr. |
| 4,438,272 A | 3/1984 | York, Jr. |
| 4,464,382 A | 8/1984 | Tanouchi et al. |
| 4,540,704 A | 9/1985 | Ueda et al. |
| 4,584,289 A | 4/1986 | Jarreau et al. |
| 4,600,724 A | 7/1986 | Sestanj et al. |
| 4,634,765 A | 1/1987 | Liu |
| 4,639,436 A | 1/1987 | Junge et al. |
| 4,652,553 A | 3/1987 | Hagmann et al. |
| 4,701,559 A | 10/1987 | Horii et al. |
| 4,734,419 A | 3/1988 | Hashimoto et al. |
| 4,771,050 A | 9/1988 | Meguro et al. |
| 4,791,126 A | 12/1988 | Tanouchi et al. |
| 4,831,045 A | 5/1989 | Tanouchi et al. |
| 4,882,315 A | 11/1989 | Chiodini et al. |
| 4,883,410 A | 11/1989 | Goddard et al. |
| 4,883,800 A | 11/1989 | Hashimoto et al. |
| 4,931,463 A | 6/1990 | Barbier et al. |
| 4,939,140 A | 7/1990 | Larson et al. |
| 4,980,357 A | 12/1990 | Goldstein et al. |
| 5,037,831 A | 8/1991 | Malamas |
| 5,066,659 A | 11/1991 | Lipinski |
| 5,091,418 A | 2/1992 | Sawada et al. |
| 5,091,524 A | 2/1992 | Vértesy et al. |
| 5,157,116 A | 10/1992 | Ducep et al. |
| 5,175,154 A | 12/1992 | Schwartz et al. |
| 5,175,186 A | 12/1992 | Barbier et al. |
| 5,192,772 A | 3/1993 | Yoshikuni et al. |
| 5,217,877 A | 6/1993 | Sawada et al. |
| 5,246,960 A | 9/1993 | Barbier et al. |
| 5,252,572 A | 10/1993 | Hermecz et al. |
| 5,270,342 A | 12/1993 | Brittain et al. |
| 5,364,636 A | 11/1994 | Ochi |
| 5,430,060 A | 7/1995 | Brittain et al. |
| 5,447,946 A | 9/1995 | Kurono et al. |
| 5,504,078 A | 4/1996 | Ducep et al. |
| 5,516,516 A | 5/1996 | Cherksey |
| 5,605,698 A | 2/1997 | Ueno |
| 5,693,327 A | 12/1997 | Shah |
| 5,698,199 A | 12/1997 | Mori et al. |
| 5,728,704 A | 3/1998 | Mylari et al. |
| 5,798,101 A | 8/1998 | Haveson |
| 5,824,668 A | 10/1998 | Rubinfeld et al. |
| 5,866,578 A | 2/1999 | Mylari et al. |
| 5,908,609 A | 6/1999 | Lee et al. |
| 6,100,048 A | 8/2000 | Cone et al. |
| 6,309,853 B1 | 10/2001 | Friedman et al. |
| 6,376,657 B1 | 4/2002 | Van Heerden et al. |
| 6,488,967 B1 | 12/2002 | Hakkinen et al. |
| 2002/0146468 A1 | 10/2002 | Rubin et al. |

FOREIGN PATENT DOCUMENTS

EP            00069439         1/1983

(Continued)

OTHER PUBLICATIONS

The Merck Manual of Diagnosis and Therapy, 17th Edition, 1999. Editor, Keryn A.G. Lane. Merck & Co., Inc., Chapter 13, "Disorders of Carbohydrate Metabolism", pp. 165-185; and p. 1902.*

Habeck M. Drug Discovery Today (Mar. 1, 2002), 7(5): 280-281. A succulent cure to end obesity.*

(Continued)

*Primary Examiner*—Michele Flood
(74) *Attorney, Agent, or Firm*—Morgan, Lewis & Bockius LLP

(57) ABSTRACT

The invention relates inter alia to pharmaceutical compositions containing an extract obtainable from a plant of the genus *Trichocaulon* or *Hoodia* having anti-diabetic activity; and to the use of such extracts and to compound (1) as herein defined and its analogues for the manufacture of medicaments having anti-diabetic activity.

19 Claims, No Drawings

FOREIGN PATENT DOCUMENTS

| | | |
|---|---|---|
| EP | 0101383 A | 2/1984 |
| EP | 0123456 | 10/1984 |
| EP | 0154639 | 9/1985 |
| EP | 0218953 | 4/1987 |
| EP | 0219156 | 4/1987 |
| EP | 0224151 | 6/1987 |
| EP | 0296574 | 12/1988 |
| EP | 0749657 | 12/1996 |
| EP | 0703731 | 4/1998 |
| EP | 1 099 444 A1 | 5/2001 |
| FR | 2 771 105 | 5/1999 |
| HU | P 99 02670 A | 2/1997 |
| HU | P 98 03039 A | 12/1998 |
| JP | 58194818 | 11/1983 |
| JP | 8832028 | 12/1996 |
| WO | WO 85 00970 | 3/1985 |
| WO | WO 90 14827 | 12/1990 |
| WO | WO 94 24149 | 10/1994 |
| WO | WO 95 00041 | 1/1995 |
| WO | WO 95 00161 | 1/1995 |
| WO | 96/39384 | 12/1996 |
| WO | 96/39385 | 12/1996 |
| WO | WO 97 15671 | 5/1997 |
| WO | 97/24369 | 7/1997 |
| WO | WO 97 47316 | 12/1997 |
| WO | WO 98 10068 | 3/1998 |
| WO | WO 98 20121 | 5/1998 |
| WO | WO 98 27113 | 6/1998 |
| WO | WO 98 28335 | 7/1998 |
| WO | 98/46243 | 10/1998 |
| WO | WO 98 42747 | 10/1998 |
| WO | WO 98/46243 | 10/1998 |

OTHER PUBLICATIONS

Davies M J et al., Diabetic Medicine (May 2004), 21(5): 403-414. Prevention of Type 2 diabetes mellitus. A review of the evidence and its application in a UK setting.*

Sturis, J et al., American J of Physiology (1995), 269(4Pt 1): E786-92. Prevention of diabetes does not completely prevent insulin secretion defects in the ZDF rat.*

Namiki et al., "Studies on the alpha-glucoside hydrolase inhibitor, adiposin", *J. Antiobiotics*, 35, pp. 1234-1236, (1982).

J. B. Clark et al., "The diabetic Zucker fatty rat", *Proc. Soc. Exp. Biol. Med.* 173, pp. 68-75, (1983).

Richard G. Peterson, "alpha-Glucosidase inhibitors in diabetes: lessons from animal studies", European Journal of Clinical Investigation, 24, Suppl. 3, 11-18 (1994).

J. H. Johnson et al., "Underexpression of beta cell high $K_m$ glucose transporters in non-insulin dependent diabetes", *Science*, 250, pp. 546-549, (1990).

Y. Lee et al., "Beta-cell lipotoxicity in the pathogenesis of non-insulin dependent diabetes mellitus of obese rats: impairment in adipocyte-beta-cell relationships", *Proc. Natl. Acad. Sci. USA*, 91(23), pp. 10878-10882, (1994).

J. L. Milburn et al., "Beta-cell GLUT-2 loss and non-insulin dependent diabetes mellitus: current status of the hypothesis", (Review) *Diabetes Metab. Rev.*, 9(3), pp. 231-236, (1993).

T. R. Pieber et al., "Amylin-insulin relationship in insulin resistance with and without diabetic hyperglycemia", *Am. J. Physiol.*, 265(3 Pt. 1), pp. E446-E453, (1993).

L. J. Slieker et al., "Glucose transporter levels in tissues of spontaneously diabetic Zucker fa/fa rat (ZDF/Drt) and viable yellow mouse ($A^{vy}$/a)", *Diabetes*, 41, pp. 187-193, (1992).

J. Sturis et al., "Alterations in pulsatile insulin secretion in the Zucker diabetic fatty rat", *Am. J. Physiol.*, (267 Endocrinol. Metab. 30), E250-259, (1994).

J.E. Friedman et al., "Altered expression of muscle glucose transporter GLUT-4 in diabetic fatty Zucker rats (ZDF/Drt-fa)," *Am. J. Physiol.*, 261 (Endocrinol. Metab. 24), E782-788 (1991).

M. Ohneda et al., "Caloric restriction in obese pre-diabetic rats prevents beta-cell depletion, loss of beta-cell GLUT-2 and glucose incompetence", *Diabetologia*, 38(2), pp. 173-179, (1995).

Peterson, Richard G., "The Zucker diabetic fatty (ZDF) rat," *Lessons from animal diabetes*, V. Ed. E. Shafrir, pp. 225-230, (1995).

Dohm, G. Lynis, et al., "Acarbose Treatment of Non-Insulin-Dependent Diabetic Fatty (ZDF/Drt-*fa*) Rats Restores Expression of Skeletal Muscle Glucose Transporter GLUT4," *Drugs in Development, vol. 1. α-Glucosidase Inhibition: Potential Use in Diabetes*, pp. 173-180 (1993).

Tschesche et al. (1964) Uber Digitanolglykoside—IX (1) Zur Konstitution des Digipurpurogenin, *Tetrahedron Letters* 9:473-480.

Smith, C. (1996) Common Names of South African Plants; Botanical Survey Memoir No. 35, pp. 34-38 (Ed. E. Percy Phillips, Estelle Van Hoepen) Department of Agricultural Technical Services (Republic of South Africa).

Oki et al. (1968) Intramolecular interaction between hydroxyl groups and carbonyl moiety in keto-alcohols, *Bulletin of the Chemical Society of Japan* 41:176-182.

Hill, B.C.F. (1969) Hoodia Gordonii, *Nat. Cact. and Succ. Journal* 24(3):69-70.

Millspaugh, C.F. (1974) American Medicinal Plants, pp 534-543, Dover Publications, Inc., New York.

Coombes, A.J. (1985) Dictionary of Plant Names, p 31. Timber Press Inc., Portland, Oregon.

Foster et al. (1990) A Field Guide to Medicinal Plants, Eastern and Central North America, pp. 136-154, Houghton Mifflin Company, Boston.

Bruyns, P. (1993) New combinations in Hoodia and Lavrania (Ascelpiadaceae—Stapelieae), *South African Journal of Botany* 59(3):342.

Swarupanandan et al. (1996) The subfamilial and tribal classification of the family Asclepiadaceae, Botanical Journal of the Linnaean Society 120:327-369.

Douketis et al. (1999) Periodic health examination, 1999 update: 1. Detection, prevention and treatment of obesity, *Canadian Medical Association Journal* 160(4):513-525.

Kopelman, P. (1999) Prescribing for obesity, *Journal of the Royal College of Physicians of London* 33(1):31-32.

Pappe, L. "A description of South African forest trees and arborescent shrubs used for technical and economical purposes" 1862 Ward & Co., London.

Laidler, P.W. "The magic medicine of the hottentots" *S. Afr. J. Sci.* 25 (1928) 433-447.

White & Sloane, "The Stapelieae" vol. 111, 2nd edition, 1937, the Abbey San Eucino Press (Pasadena), pp 1000-1002.

Tschesche, R. et al. "Uber pflanzliche Herzgifte, XXX. Mitteil. : Neue Glykoside aus den Blattern von *Digitalis purpurea* und *Digitalis lanata" Chemische Berichte* 88 (1955) 1569-1576.

The Medicinal and Poisonous Plants of Southern and Eastern Africa, J M Watt, MG Breyer-Brandwijk, Second Edition, 1962, p. 138.

Heller, M. et al. "Electrophilic Addition to the delta-14 Double Bond of a Steriods" *Steroids* 3 (1964) 193-201.

Mitsuhashi, H. et al. "Studies on the Constituents of Asclepiadacae plants. XIII. Epimerization at C-17 and Optical Rotatory Dispersion Study of C/D Cis Pregnane2one Derivatives" *Steroids* 4 (1964) 483-493.

Borowski, E. et al. "Chemical Studies on Amphotericin B. II. 2-methylheptadecanedioic acid from perhydrogenated amphoteron B" *Tetrahedron Letters* 9 (1965) 473-478.

Mitsuhashi, H. et al. "Constituents of Asclepiadaceae plants. XVI. Components of *Metaplexis japonica*" *Chem. Pharm. Bull.* 13 (1965) 1332-1340.

Mitsuhashi, H. et al. "Constituents of Asclepiadaceae plants. XVI. Components of *Metaplexis japonica*" *Chemical Abstracts* 65 (1966) XP002084116.

Nikaido, H. et al. "Components of *Bouceriosa aucheriana* DECNE" *Chem. Pharm. Bull.* 15 (1967) 725-726.

Tschesche, R. et al. "Uber Digitanalglykoside, 15. Synthese von 12.alpha.20R-Epoxy-5.alpha.,14.beta.,beta-H-pregnanen" *Chemische Berichte* 100 (1967) 464-479.

Oki, M. et al. "Intramolecular interaction between hydroxyl groups and carbonyl moiety in keto-alcohols" *Bulletin of the Chemical Society of Japan* 41 (1968) 176-182.

Mitsuhashi, H. et al. "Constituents of Asclepiadaceae plants. XXV. Components of *Cynanchum boerhavifolium*" *Yagugaku Zasshi* 89 (1969) 1352-1357.

Mitsuhashi, H. et al. "Constituents of Asclepiadaceae plants. XXV. Components of *Cynanchum boerhavifolium*" *Chemical Abstracts* 72 (1970) XP002084115.

Yoshii E. et al. "Preg-14-en-20-ones. Facile preparation and 14.beta-hydroxylation" *Chemical Abstracts* 77 (1972) XP002084118, abstracting *Chem. Pharm. Bull.* 20 (1972) 1827-1829.

Bando, H. et al. "Constituents of Asclepiadacaea plants. XXXI. Component of *Stapelia grandiflora*" *Chem. Pharm. Bull.* 22 (1974) 1209-1211.

Bruyns, P.V. "Notes on Trichocaulon and Hoodia" Nat. Cact. & Succ. J. 35 4 (1980) 102-106.

De Rick, A. et al. "Digoxin-quinidine interaction in the dog" *J. Vet Pharmacol. Ther.* 43 (1981) 215-218.

Namiki, Shinjuro et al. "Studies on the a-glucoside hydrolase inhibitor, adiposin. I. Isolation and Physicochemical properties" *The Journal of Antibiotics* 35 (1982) 1234-1236.

Wada, et al. "Studies on the constituents of Ascepiadaceae plants. L. Two new oligoglycosides, cynanchoside C2 and cynanchoside CI, from *Cynanchum caudatum Max.*" *Chem. Pharm. Sci.* 30 (1982) 3500-3504.

Dolle. R.E. et al. "Total synthesis of elfamycins: aurodox and efrotomycin. 1. Strategy and construction of key intermediates" *J. Am. Chem. Soc.* 107 (1985) 1691-1694.

Dolle, R.E. et al. "Total synthesis of elfamycins: aurodox and efrotomycin. 2. Coupling of key intermediates and completion of the synthesis" *J. Am. Chem. Soc.* 107 (1985) 1695-1698.

Habermehl, G.G. et al. "Rearrangement of 14.beta.-hydroxy-12.beta.-sulfoxy steroids to 13,17-seco-12,17-cyclosteroids; a 2D-NMR analysis" *Z. Naturforsch.* 40b (1985) 656-660.

Deepak, D. et al. "A new pregnane glycoside from *Periploca calophylla*" *Indian Journal of Chemistry, Section B* 25b (1986) 44-45.

Templeton, J.F. et al. "Progesterone Derivatives That Bind to the Digitalis Receptor: Synthesis of 14.beta-Hydroxyprogesterone. A Novel Steroid with Positive Inotropic Activity" *J Med. Chem.* B 30 (1987) 1502-1505.

Hayashi, K. et al. "Four pregnane glycosides, boucerosides AI, AII, BI and BII, from *Boucerosia aucheriana*" *Phytochemistry* 27 (1988) 3919-3924.

Trivedi, R. et al. "A pregnane ester oligoglycoside form *Oxystelma esculentum*" *Phytochemistry* 28 (1989) 1211-1213.

Tanaka, T. et al. "Studies on the constituents of Asclepiadaceae plants. Part 71. Pregnane glycosides from *Boucerosia aucheriana*" *Phytochemistry* 29 (1990) 229-237.

Chen, J. et al. "A novel C2 I steroidal glycoside from *Marsdenia incisa*" *Chemical Abstracts* 115 (1991) XP002084119.

Chen, J. et al. "A novel C21 steroidal glycoside from *Marsdenia incisa*" Yunnan Zhiwu Yanjiu 13 (1991) 231-232.

Glendinning, J.I. "Effectiveness of cardenolides as feeding deterrents to *Peromyscus mice*" *Chemical Abstracts* 117 (1992) XP002084117.

Glendinning, II. "Effectiveness of cardenolides as feeding deterrents to *Peromyscus mice*" *J Chem. Ecol.* 18 (1992) 1559-1575.

Plowes, D.C.H. "A Preliminary Reassessment of the Genera Hoodia and Triehocaulon (Stapelieae: Ascelpiadaceae)" *Asklepios* 56 (1992) 5-15.

Bruyns, P. "A Revision of Hoodia and Lavrania (Asceepiadaceae—Stapelieae)" *Botanische Jahrbucher fur systematik Pflanzengeschichte and Pflanzengeographie* 1152 (1993) 145-270.

Miwa H, et al. "Structural determinants of the melanocortin peptides required for activation of meianocortin-3 and melanocorin-4 receptors" *Journal of Pharmacology and Experimental Therapeutics* 273 (1995) 367-372.

Chen S.W. et al. "The hyperphagic effect of 3.alpha-hydroxylated pregnane steroids in male rats" *Pharmacology, Biochemistry and Behaviour* 53 (1996) 777-782.

von Koenen, Eberhard "Heil-, Gift- and eßbare Pflanzen in Namibia" Klaus Hess Verlag 1996. p. 131, entry No. 293.

Yoshikawa, K. et al. "Steroidal glyosides from the fresh stem of *Stephanotis lutchuensis var. japonica* (Asclepiadaceae). Chemical structures of stephanosides A-J" *Chem. Pharm. Bull.* 44 (1996) 1790-1796.

Yoshikawa, K. et al. "Steroidal glyosides from the fresh stem of *Stephanotis lutchuensis var. japonica* (Asclepiadaceae). Chemical structures of stephanosides K-Q" *Chem. Pharm. Bull.* 44 (1996) 2243-2248.

Haskell-Luevano, C, et al. "Discovery of Prototype Peptidomirnetic Agonists at the Human Melanocortin Receptors MCIR and MC4R" *J. Med. Chem.* 40 (1997) 2133-2139.

Huszar, D. et al. "Targeted Disruption of the Melanocortin-4 Receptor Results in Obesity in Mice" *Cell* 88 (1997) 131-141.

Fan, W. et al. "Role of melanocortinergic neurons in feeding and the *agouti* obesity syndrome" *Nature* 385 (1997) 165-168.

Barnett, A. "In Africa the Hoodia cactus keeps men alive. Now its secret is stolen to make us thin." The Observer 17 Jun. 2001.

Tulp, Orien Lee et al. "Effect of Hoodia Plant on Food Intake and Body Weight in Lean and Obese LA/Ntul//cp Rats"

*Experimental Biology* 2001 ® Abstracts 2.1-537.42 Part 1338.5.
Hargreaves, B. and Queen Turner "Uses and Misuses of Hoodia" *Askelpios* 86 (2002) 11-16.
"Stomach staples, gastric bypass ops, power-assisted liposuction . . . " The Telegraph Feb. 14, 2004.
Thunberg, Charles Peter "Travels in Europe, Africa and Asia made between the years 1770 and 1779," vol. 2., F. and C. Rivington 1795, pp. 140, 171.

Warburg, Otto "Die Pflazenwelt, Dritter Band" Bibliographisches Institut Leipzig 1922, p. 146 (translation of highlighted section attached).
Marloth, R. "The Flora of South Africa with synopsis of the South African genera of Phanerogamous plants" vol. III, pp. 1000-1002, Wheldon & Wesley, London 1932.

* cited by examiner

EXTRACTS, COMPOUNDS AND PHARMACEUTICAL COMPOSITIONS HAVING ANTI-DIABETIC ACTIVITY AND THEIR USE

CROSS-REFERENCE TO RELATED APPLICATIONS

This application claims benefit of priority 35 U.S.C 119 to U.K. Application No. 0016213.1 filed Jun. 30, 2000 and is incorporated herein in its entirety by reference.

FIELD OF THE INVENTION

THIS INVENTION relates to a new use for steroidal glycosides and compositions containing them for use in the prevention and treatment of diabetes.

In a particular application, the invention relates to an anti-diabetic agent, to an anti-diabetic composition containing the anti-diabetic agent, and to a method for treating diabetes.

DESCRIPTION OF THE RELATED ART

The International application WO 98/46243 discloses steroidal glycosides having appetite suppressant activity. In particular, it describes extracts from the genus *Trichocaulon* or of the genus *Hoodia* and having appetite suppressant activity; these extracts include the compound of general formula (1):

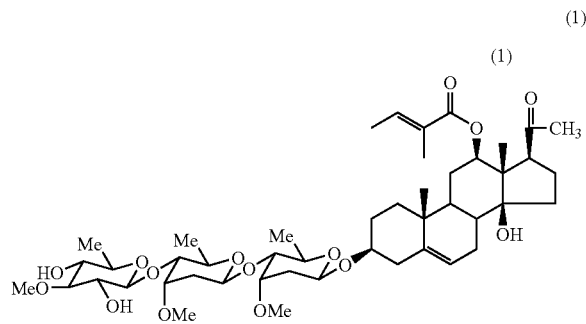

In accordance with S.I. nomenclature, the active principle (1) is the compound 3-0-[-β-D-thevetopyranosyl-(1→4)-β-D-cymaropyranosyl-]-12β-0-tigloyloxy-14-hydroxyl-14β-pregn-50-en-20-one ($C_{47}H_{74}O_{15}$ $M^+878$).

Also, WO 98/46243 discloses further active analogues or steroidal glycosides derivatives of general formula (2), (3), (4), (5), (6), (7), (8), (9), (10), (11), (14) (see herein below) having appetite suppressant activity.

Diabetes is a deficiency condition marked by a habitual discharge of an excessive quantity of urine; in particular, it includes diabetes mellitus, which is a metabolic disorder in which the ability to oxidize carbohydrates is more or less completely lost, usually due to faulty pancreatic activity, especially of the islets of Langerhans, and consequent disturbance of normal insulin mechanism. This produces hyperglycemia with resulting glycosuria and polyuria giving symptoms of thirst, hunger, emaciation and weakness and also imperfect combustion of fats with resulting acidosis, sometimes leading to dyspnea, lipemia, ketonuria, and finally coma; there may also be pruritus and lowered resistance to pyogenic infections (Dorland's Medical Dictionary—24th Edition—W.B.Saunders Company).

The diabetic disease state is characterized by an impaired glucose metabolism that manifests itself in, inter alia, elevated glucose levels in patients suffering therefrom. Generally, diabetes is classified into two distinct subgroups:

(1) Type 1 diabetes, or insulin-dependent diabetes mellitus (IDDM), which arises when patients lack β-cells producing insulin in their pancreatic glands, and (2) Type 2 diabetes, or non-insulin dependent diabetes mellitus (NIDDM), which occurs in patients with, inter alia, impaired β-cell function.

At present, Type 1 diabetic patients are treated with insulin, while the majority of Type 2 diabetic patients are treated with hypoglycemic agents, such as sulfonylureas that stimulate β-cell function, with other agents that enhance the tissue selectivity of the patients towards insulin, or with insulin itself. Unfortunately, the use of insulin currently requires multiple daily doses, normally administered by self-injection, with determination of the proper dosage of insulin requiring frequent estimations of the sugar in urine or blood, performed either by the patient or the administering physician. The unintended administration of an excess dose of insulin can result in hypoglycemia, with adverse effects ranging from mild abnormalities in blood glucose to coma, or even death. Although hypoglycemic agents such as sulfonylureas have been employed widely in the treatment of NIDDM, this treatment is, in many instances, not completely satisfactory. Where existing treatments prove ineffective in normalizing blood sugar levels of patients, there is an increased risk of acquiring diabetic complications. Also, many patients gradually lose the ability to respond to treatment with sulfonylureas and are thus gradually forced into insulin treatment. Since many extant forms of diabetic therapy have proven ineffective achieving satisfactory glycemic control, there continues to be a great demand for novel therapeutic approaches.

SUMMARY OF THE INVENTION

According to the invention, it has been found that the extracts from a plant of the genus *Trichocaulon* or of the genus *Hoodia*, the compound of general formula (1), as well as the steroidal glycosides derivatives of general formula (2), (3), (4), (5), (6), (7), (8), (9), (10), (11), (12), (13), (14) (see herein below) have anti-diabetic activity.

The present invention is particularly concerned with the treatment of Type II diabetes and the corresponding anti-diabetic agents. The invention provides a new use for steroidal glycosides and compositions containing them for use in the prevention and treatment of diabetes. The invention provides an anti-diabetic agent, an anti-diabetic composition containing the anti-diabetic agent, a foodstuff or beverage containing the anti-diabetic agent, kits based on the anti-diabetic agent, a method for preventing or treating diabetes or impaired glucose tolerance, and a method of decreasing blood glucose level. The anti-diabetic agent may be an extract from a plant of the genus *Trichocaulon* or of the genus *Hoodia*, a compound of general formula (1), as well as the steroidal glycosides derivatives of general formula (2), (3), (4), (5), (6), (7), (8), (9), (10), (11), (12), (13), or (14), each as described herein below.

DETAILED DESCRIPTION OF THE INVENTION

Definitions

"Acyl" means an H—CO— or Alkyl-CO-group wherein the alkyl group is as herein described. Preferred acyls contain a lower alkyl. Exemplary acyl groups include formyl, acetyl, propanoyl, 2-methylpropanoyl, butanoyl and palmitoyl.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. Exemplary alkyl groups include methyl, ethyl, n-propyl, i-propyl, n-butyl, t-butyl, n-pentyl, 3-pentyl.

"Aryl" means an aromatic monocyclic or multicyclic ring system of about 6 to about 14 carbon atoms, preferably of about 6 to about 10 carbon atoms. The aryl is optionally substituted with one or more ring system substituents which may be the same or different, and are as defined herein. Exemplary aryl groups include phenyl or naphthyl, or phenyl substituted or naphthyl substituted.

The term "pharmaceutical composition" means a composition comprising a compound of general formula (1), (2), (3), (4), (5), (6), (7), (8), (9), (10), (11), (12), ((13), (14), or an extract in accordance with this invention, and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

"Pharmaceutically acceptable" means it is, within the scope of sound medical judgement, suitable for use in contact with the cells of humans and animals without undue toxicity, irritation, allergic response and the like, and are commensurate with a reasonable benefit/risk ratio.

"Pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington, Pharmaceutical Sciences, Mack Publishing Co., Easton, Pa., latest edition.

"Pharmaceutically acceptable prodrugs" as used herein means those prodrugs of the compounds useful according to the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. Because of the ease with which the metabolically cleavable groups of the compounds useful according to this invention are cleaved in vivo, the compounds bearing such groups act as pro-drugs. A thorough discussion of prodrugs is provided in the following: Design of Prodrugs, H. Bundgaard, ed., Elsevier, 1985; Methods in Enzymology, K. Widder et al, Ed., Academic Press, 42, p.309–396, 1985; A Textbook of Drug Design and Development, Krogsgaard-Larsen and H. Bundgaard, ed., Chapter 5; Design and Applications of Prodrugs p.113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

"Pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. See, for example S. M. Berge, et al., Pharmaceutical Salts, J. Pharm. Sci., 66: p.1–19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts.

The term "animal" as used herein extends to, but is not restricted to, companion animals, e.g. household pets and domesticated animals; non-limiting examples of such animals include cattle, sheep, ferrets, swine, camels, horses, poultry, fish, rabbits, goats, dogs and cats.

According to the present invention, and as hereinbefore and hereafter mentioned:

"diabetes" preferably refers to non-insulin dependent diabetes (type II);

"anti-diabetic" means the activity useful for the "treatment" of "diabetes", which includes the prevention of the development of diabetes, and/or the treatment of established diabetes; it also includes the prevention of the causes of diabetes, and/or the decrease or disappearance of its symptoms and/or consequences.

In particular, it has been found that compounds of the invention have at least the following double therapeutic effect:

1) the prevention of diabetes, since the compounds of the invention can treat impaired glucose tolerance;

2) the actual treatment of established diabetes since the compounds of the invention can decrease the blood glucose level.

According to a first embodiment, the invention concerns the use of an extract from a plant of the genus *Trichocaulon* or *Hoodia*, as described in WO 98/46243 (the contents of which are incorporated herein by reference thereto) in the manufacture of a medicament having anti-diabetic activity.

Preferably, the said extract comprises as an active ingredient a compound of general formula (1):

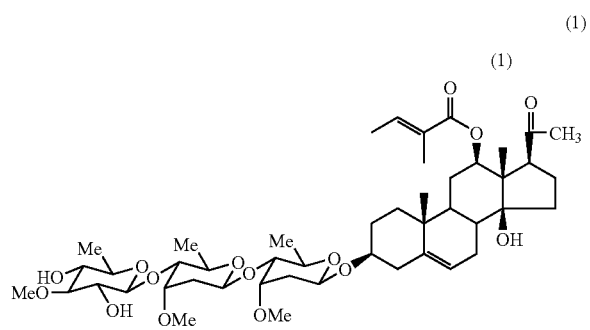

(1)

and/or a pharmaceutically acceptable salt or prodrug thereof.

According to a further aspect, the invention also concerns the said extract for use as a medicament having anti-diabetic activity.

The invention also extends to a pharmaceutical composition having anti-diabetic activity comprising an effective quantity of the said extract; and to compounds of formula (1) having anti-diabetic activity.

It is also provided a method for treating diabetes by administering to a human or animal an effective dosage of the said extract or the said composition.

According to a still further aspect, the invention also concerns the use of the said extract in the manufacture of a foodstuff or beverage to have an anti-diabetic effect when ingested.

The said foodstuff or beverage comprising an effective quantity of the said extract to have an anti-diabetic effect when ingested is also part of the present invention.

According to a further embodiment, the invention concerns the use of one or more steroidal glycosides derivatives of general formula (A) (see below) and their pharmaceutically acceptable salts and pro-drugs in the manufacture of a medicament having anti-diabetic activity:

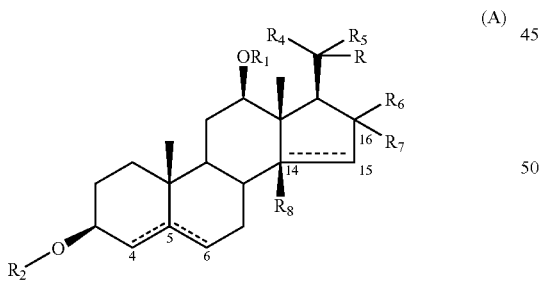

(A)

In the general formula (A):
R=alkyl;
$R_1$=H, alkyl, tigloyl, anthraniloyl, or any other organic ester group;
$R_2$=H, or one or more 6-deoxy carbohydrates, or one or more 2,6-dideoxy carbohydrates, or glucose molecules, or combinations thereof;
$R_3$=H, alkyl, aryl, acyl, or glucoxy;
$R_4$, $R_5$=either $R_4$, $R_5$ form together with the Carbon atom which they are attached to a carbonyl group (—C=O), or $R_4$=H and $R_5$=H, OH;

$R_6$, $R_7$=either $R_6$, $R_7$ form together with the Carbon atom C-16 which they are attached to a carbonyl group (—C=O), or $R_6$=H and $R_7$=—$OR_3$;
$R_8$=H, OH;
and
the broken lines indicate the optional presence of a further bond between C4–C5 or C5–C6, and/or C14–C15.

Preferably, compounds of general formula (A) can be chosen from the following families of formula (2), (3), (4), (5), (6), (7), (8), (9), (10), (11), (12), (13), or (14), below, as described in WO 98/46243 and incorporated herein by reference:

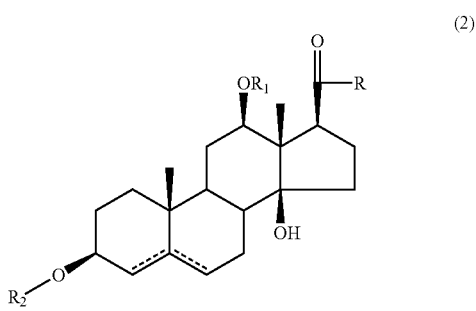

(2)

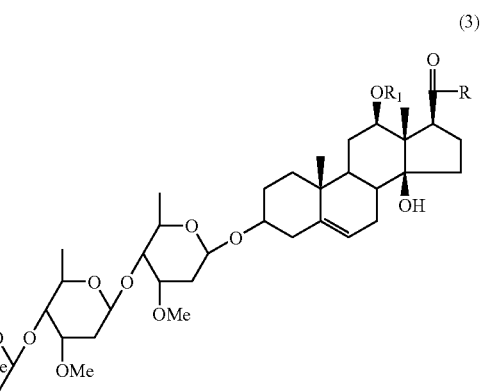

(3)

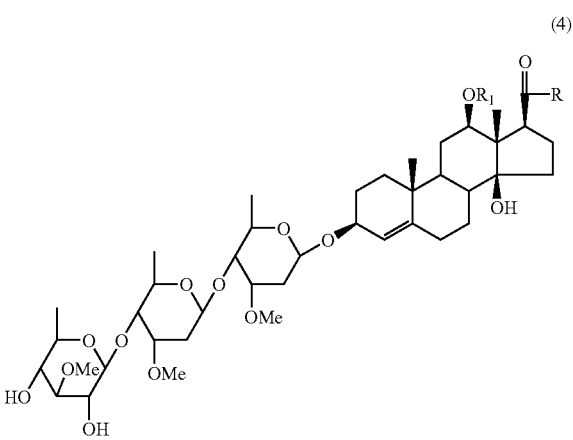

(4)

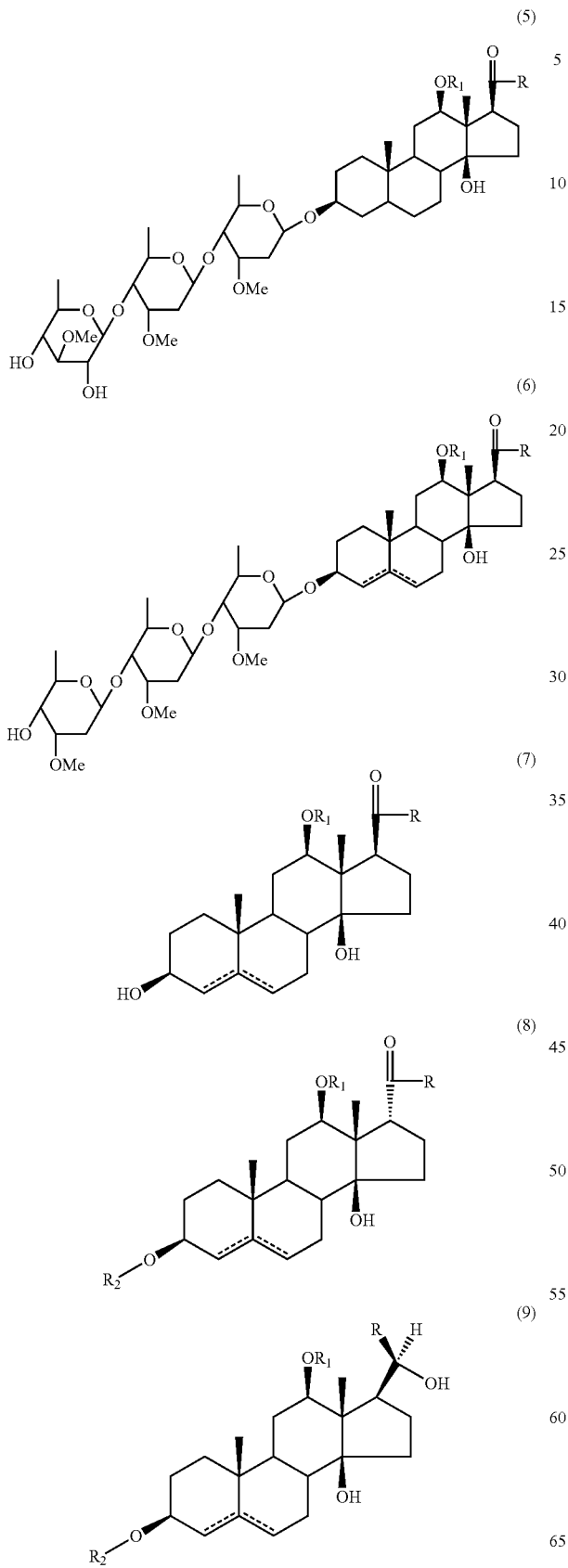
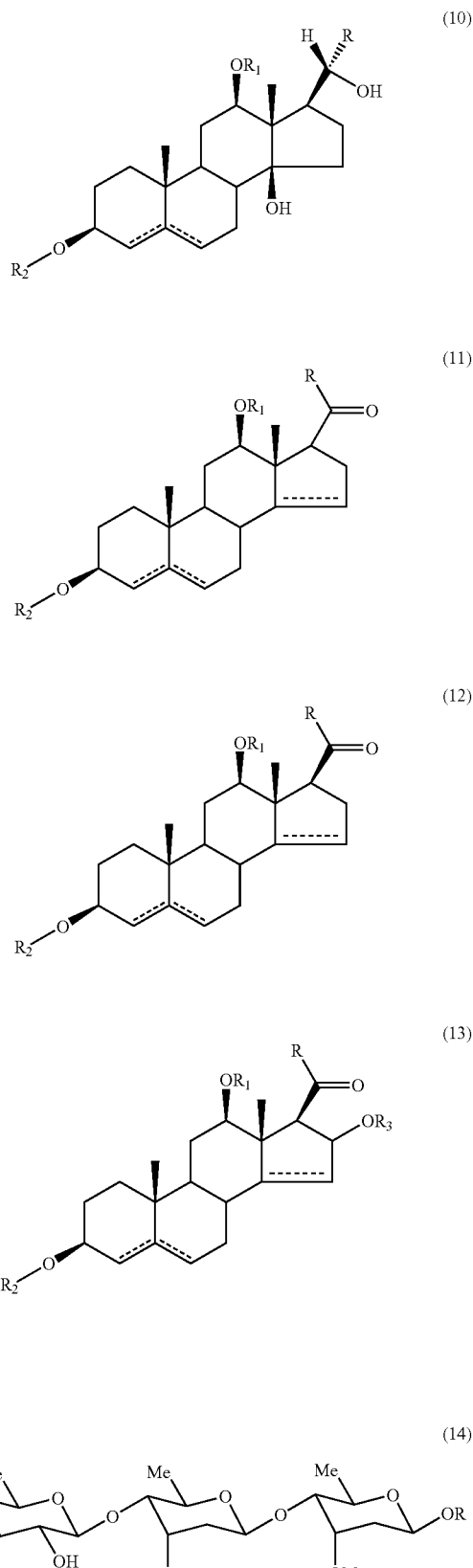

and their pharmaceutically acceptable salts and pro-drugs.

In the general formula (2), (3), (4), (5), (6), (7), (8), (9), (10), (11), (12), (13), above: R, $R_1$, $R_2$, $R_3$ are as defined above;

and in the general formula (14): R=H, alkyl, aryl or any steroid possessing a C14 beta hydroxy group, or a C12 beta hydroxy functionality, or a C17 acyl group, or a C5–C6 olefin, or combinations thereof, as described in WO 98/46243.

According to a still more preferred aspect, compounds of general formula (A) are represented by formula (1):

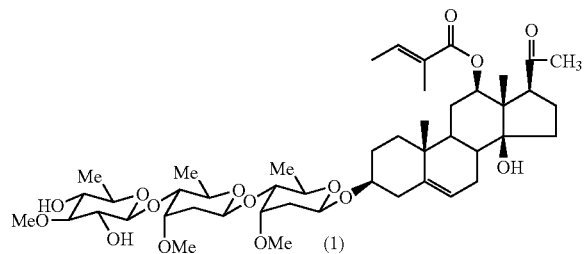

and its pharmaceutically acceptable salts and pro-drugs.

According to a preferred embodiment, the invention concerns the use of the compound of general formula (1) (see herein above) as described in WO 98/46243 and incorporated herein by reference in the manufacture of a medicament having anti-diabetic activity.

According to a further aspect, the invention also concerns the said compounds of general formula (A), including that of formula (1) (see herein above) for use as a medicament having anti-diabetic activity.

The invention also extends to a pharmaceutical composition having anti-diabetic activity comprising an effective quantity of one or more of the said compounds of general formula (A), preferably that of formula (1) (see herein above).

It is also provided a method for treating diabetes by administering to a human or animal an effective dosage of one or more of the said derivatives of general formula (A), preferably that of formula (1) (see herein above) or the said compositions.

According to a still further aspect, the invention also concerns the use of one or more of the said derivatives of general formula (A), preferably that of formula (1), (see herein above) in the manufacture of a foodstuff or beverage to have an anti-diabetic effect when ingested.

The said foodstuff or beverage comprising an effective quantity of one or more of the said derivatives of general formula (A), preferably that of formula (1)(see herein above) to have an anti-diabetic effect when ingested, is also part of the present invention.

As described in WO 98/46243 and incorporated herein by reference, the active ingredient may be an extract from a plant of the genus *Trichocaulon* or *Hoodia*, or a compound of the formula (1) (either extracted from a plant of the genus *Trichocaulon* or *Hoodia* or prepared synthetically) or a derivative thereof.

The plant may be of the species *Trichocaulon officinale* or *Trichocaulon piliferum*, or the species *Hoodia currorii*, *Hoodia gordonii* or *Hoodia lugardii*.

Preferably, the compounds of the invention are prepared in pharmaceutically acceptable dosage forms. The anti-diabetic composition or formulation may consist of the anti-diabetic agent admixed with a pharmaceutical excipient, diluent or carrier. Other suitable additives, including a stabilizer and such other ingredients as may be desired may be added.

The composition may be prepared in unit dosage form.

As an anti-diabetic agent, a compound of formula (A), preferably of formula (1), or the composition as herein above mentioned, is advantageously administered to said human in a dosage amount of from about 0.05 mg/kg/day to about 100 mg/kg/day. A preferred dosage range is about 0.1 mg/kg/day to about 50 mg/kg/day. When using the spray dried powder form of the extract of this invention, a preferred dosage range is about 0.5 mg/kg/day to about 100 mg/kg/day; especially preferred is about 1 mg/kg/day to about 50 mg/kg/day.

According to a further aspect, the invention also concerns a pharmaceutical composition comprising an effective amount of:

i) an extract as mentioned above or a compound of formula (A), (1), (2), (3), (4), (5), (6), (7), (8), (9), (10), (11), (12), (13) or (14) as described above, in association with ii) one or more other agents chosen from: representative agents to treat diabetes, glycogen phosphorylase inhibitors, sorbitol dehydrogenase inhibitors, glucosidase inhibitors, aldose reductase inhibitors;

Representative agents that can be used to treat diabetes include insulin and insulin analogs: (e.g., LysPro insulin, inhaled formulations comprising insulin); GLP-1 (7-37) (insulinotropin) and GLP-1 (7-36)-$NH_2$; sulfonylureas and analogs: chlorpropamide, glibenclamide, tolbutamide, tolazamide, acetohexamide, glypizide, glimepiride, repaglinide, meglitinide; biguanides: metformin, phenformin, buformin; a2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; glitazones: ciglitazone, pioglitazone, englitazone, troglitazone, darglitazone, rosiglitazone; PPAR-gamma agonists; RXR agonists: JTT-501, MCC-555, MX-6054, DRF2593, GI-262570, KRP-297, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; β-agonists: BRL 35135, BRL 37344, Ro 16–8714, ICI D7114, CL 316,243, TAK-667, AZ40140; phosphodiesterase inhibitors, both cAMP and cGMP type: sildenafil, L686398: L-386,398; lipid-lowering agents: benfluorex, atorvastatin; anti-obesity agents: fenfluramine, orlistat, sibutramine; vanadate and vanadium complexes (e.g., Naglivan®) and peroxovanadium complexes; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER1741 1, TER17529; gluconeogenesis inhibitors:GP3034; somatostatin analogs and antagonists; antilipolytic agents: nicotinic acid, acipimox, WAG 994; glucose transport stimulating agents: BM-130795; glycogen phosphorylase inhibitors: glucose synthase kinase inhibitors: lithium chloride, CT98014, CT98023; galanin receptor agonists; MTP inhibitors such as those disclosed in U.S. provisional patent application No. 60/164,803; growth hormone secretagogues such as those disclosed in PCT publication numbers WO 97/24369 and WO 98/58947; NPY antagonists: PD-160170, BW-383, BW1229, CGP-71683A, NGD 95-1, L-152804; anorectic agents inlcuding 5-HT and 5-HT2C receptor antagonists and/or mimetics: dexfenfluramine, Prozac®, Zoloft®; CCK receptor agonists: SR-27897B; galanin receptor antagonists; MCR-4 antagonists: HP-228; leptin or mimetics:leptin; 11-beta-hydroxysteroid dehydrogenase type-I inhibitors; urocortin mimetics, CRF antagonists, and CRF binding proteins: RU-486, urocortin. Other anti-diabetic agents that can be used include ergoset and D-chiroinositol. Other anti-diabetic agents will be known to those skilled in the art.

Any glycogen phosphorylase inhibitor may be used as the second compound of this invention. The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described hereinafter). A variety of these compounds are included in the following published PCT patent applications: PCT application publication WO 96/39384 and WO96/39385. However, other glycogen phosphorylase inhibitors will be known to those skilled in the art.

Any sorbitol dehydrogenase inhibitor may be used as the second compound of the invention. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. No's. 5,728,704 and 5,866,578 disclose compounds and a method for treating or preventing diabetic complications by inhibiting the enzyme sorbitol dehydrogenase.

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom.

Any glucosidase inhibitor may be employed in combination with the extracts of this invention and with the compounds of Formula (A), the stereoisomers and prodrugs thereof, and the pharmaceutically acceptable salts of the compounds, stereoisomers, and prodrugs; however, generally preferred glucosidase inhibitors comprise amylase inhibitors. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase inhibitors will be known to one of ordinary skill in the art. However, in the practice of the pharmaceutical compositions, combinations, methods, and kits of the instant invention, generally preferred glucosidase inhibitors are those inhibitors selected from the group consisting of acarbose, adiposine, voglibose, miglitol, emiglitate, MDL-25637, camiglibose, tendamistate, AI-3688, trestatin, pradimicin-Q and salbostatin.

The glucosidase inhibitor acarbose, O-4,6-dideoxy-4-[[(1S,4R,5S,6S)-4,5,6-trihydroxy-3-(hydroxymethyl)-2-cyclohexen-1yl]-amino]-α-glucopyranosyl-(1→4)-O-α-D-glucopyranosyl-(1→4)-D-glucose, the various amino sugar derivatives related thereto and a process for the preparation thereof by the microbial cultivation of *Actinoplanes* strains SE 50 (CBS 961.70), SB 18 (CBS 957.70), SE 82 (CBS 615.71), SE 50/13 (614.71) and SE 50/110 (674.73) are disclosed in U.S. Pat. No's. 4,062,950 and 4,174,439 respectively.

The glucosidase inhibitor adiposine, consisting of adiposine forms 1 and 2, is disclosed in U.S. Pat. No. 4,254,256. Additionally, a process for the preparation and purification of adiposine is disclosed in Namiki et al., J. Antiobiotics, 35, 1234–1236 (1982). The glucosidase inhibitor voglibose, 3,4-dideoxy-4-[[2-hydroxy-1-(hydroxymethyl) ethyl]amino]-2-C-(hydroxymethyl)-D-epi-inositol, and the various N-substituted pseudo-aminosugars related thereto, are disclosed in U.S. Pat. No. 4,701,559.

The glucosidase inhibitor miglitol, (2R,3R,4R,5S)- 1-(2-hydroxyethyl)-2-(hydroxymethyl)-3,4,5-piperidinertol, and the various 3,4,5-trihydroxypiperidines related thereto, are disclosed in U.S. Pat. No. 4,639,436.

The glucosidase inhibitor emiglitate, ethyl p-[2-[(2R,3R,4R,5S)-3,4,5-trihydroxy-2-(hydroxymethyl)piperidino] ethoxy]-benzota, the various derivatives related thereto and pharmaceutically acceptable acid addition salts thereof, are disclosed in U.S. Pat. No. 5,192,772.

The glucosidase inhibitor MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor camiglibose, methyl 6-deoxy-6-[(2R,3R,4R,5S)-3,4,5-trihydroxy-2-(hrdroxymethyl)piperidino]β-D-glucopyranoside sesquihydrate, the deoxynojirimycin derivatives related thereto, the various pharmaceutically acceptable salts thereof and synthetic methods for the preparation thereof, are disclosed in U.S. Pat. Nos. 5,157,116 and 5,504,078.

The glucosidase inhibitor pradimicin-Q and a process for the preparation thereof by the microbial cultivation of *Actinomadura verrucospora* strains R103-3 or A10102, are disclosed in U.S. Pat. Nos. 5,091,418 and 5,217,877 respectively.

The glycosidase inhibitor salbostatin, the various pseudosaccharides related thereto, the various pharmaceutically acceptable salts thereof and a process for the preparation thereof by the microbial cultivation of *Streptomyces albus* strain ATCC 21838, are disclosed in U.S. Pat. No. 5,091,524.

Any aldose reductase inhibitor may be used in the pharmaceutical compositions, methods and kits of this invention. The term aldose reductase inhibitor refers to a compound which inhibits the bioconversion of glucose to sorbitol catalyzed by the enzyme aldose reductase. Such inhibition is readily determined by those skilled in the art according to standard assays (J. Malone, *Diabetes*, 29:861–864, 1980. "Red Cell Sorbitol, an Indicator of Diabetic Control"). The following patents and patent applications, each of which is hereby wholly incorporated herein by reference, exemplify aldose reductase inhibitors which can be used in the compositions, methods and kits of this invention, and refer to methods of preparing those aldose reductase inhibitors: U.S. Pat. No. 4,251,528; U.S. Pat. No. 4,600,724; U.S. Pat. No. 4,464,382, U.S. Pat. No. 4,791,126, U.S. Pat. No. 4,831,045; U.S. Pat. No. 4,734,419; 4,883,800; U.S. Pat. No. 4,883,410; U.S. Pat. No. 4,883,410; U.S. Pat. No. 4,771,050; U.S. Pat. No. 5,252,572; U.S. Pat. No. 5,270,342; U.S. Pat. No. 5,430,060; U.S. Pat. No. 4,130,714; U.S. Pat. No. 4,540,704; U.S. Pat. No. 4,438,272; U.S. Pat. No. 4,436,745, U.S. Pat. No. 4,438,272; U.S. Pat. No. 4,436,745, U.S. Pat. No. 4,438,272; U.S. Pat. No. 4,436,745,U.S. Pat. No. 4,438,272; U.S. Pat. No. 4,980,357; U.S. Pat. No. 5,066,659; U.S. Pat. No. 5,447,946; U.S. Pat. No. 5,037,831.

A variety of aldose reductase inhibitors are specifically described and referenced below, however, other aldose reductase inhibitors will be known to those skilled in the art. Also, common chemical USAN names or other designations are in parentheses where applicable, together with reference to appropriate patent literature disclosing the compound.

Accordingly, examples of aldose reductase inhibitors useful in the compositions, methods and kits of this invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy- 1 -naphthalenyl]thioxomethyl}-N-methylglycine (tolrestat, U.S. Pat. No. 4,600,724);
3. 5-[(Z,E)- β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);
4. 3-(4-bromo-2-fluorobenzyl)-7-chloro-3,4-dihydro-2,4-dioxo- 1(2H)-quinazolineacetic acid (zenarestat, U.S. Pat. No. 4,734,419, and U.S. Pat. No. 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H- 1,4-benzothiazine-2acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060);
10. (S)-6-fluorospiro[chroman-4,4'-imidazolidine]-2,5¢-dione (sorbinil, U.S. Pat. No. 4,130,714);
11. d-2-methyl-6-fluoro-spiro(chroman-4',4'-imidazolidine)-2', 5'-dione (U.S. Pat. No. 4,540,704);
12. 2-fluoro-spiro(9H-fluorene-9,4'-imidazolidine)-2',5'-dione (U.S. Pat. No. 4,438,272);
13. 2,7-di-fluoro-spiro(9H-fluorene-9,4'-imidazolidine)-2', 5'-dione (U.S. Pat. No. 4,436,745, U.S. Pat. No .4,438,272);
14. 2,7-di-fluoro-5-methoxy-spiro(9H-fluorene-9,4'-imidazolidine)-2',5'-dione (U.S. Pat. No. 4,436,745, U.S. Pat. No. 4,438,272);
15. 7-fluoro-spiro(5H-indenol[1,2-b]pyridine-5,3'-pyrrolidine)-2,5'-dione (U.S. Pat, No, 4,436,745, U.S. Pat. No. 4,438,272);
16. d-cis-6'-chloro-2',3'-dihydro-2'-methyl-spiro-(imidazolidine-4,4'-4'H-pyrano(2,3-b)pyridine)-2,5-dione (U.S. Pat No. 4,980,357);
17. spiro[imidazolidine-4,5'(6H)-quinoline]-2,5-dione-3'-chloro-7', 8'-dihydro-7',8'-dihydro-7'-methyl-(5-'-cis) (U.S. Pat. No. 5,066,659);
18. (2S,4S)-6-fluoro-2',5'-dioxospiro(chroman-4,4'-imidazolidine)-2-carboxamide (fidarestat, U.S. Pat. No. 5,447,946); and
19. 2-[(4-bromo-2-fluorophenyl)methyl]-6-fluorospiro [isoquinoline-4(1H),3'-pyrrolidine]-1,2',3,5' (2H)-tetrone (minalrestat, U.S. Pat. No. 5,037,831).

Other aldose reductase inhibitors include compounds of formula (B):

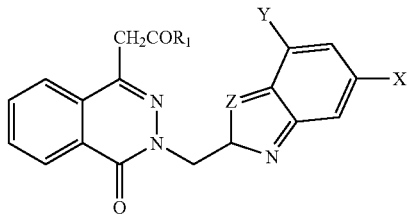

and pharmaceutically acceptable salts thereof, wherein

Z in the compound of formula B is O or S;

$R^1$ in the compound of formula B is hydroxy or a group capable of being removed in vivo to produce a compound of formula B wherein $R^1$ is OH; and X and Y in the compound of formula B are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of formula B:

20. 3,4-dihydro-3-(5-fluorobenzothiazol-2-ylmethyl)-4-oxophthalazin-1-yl-acetic acid [$R^1$=hydroxy; X=F; Y=H];
21. 3-(5,7-difluorobenzothiazol-2-ylmethyl)-3,4-dihydro-4-oxophthalazin-1-ylacetic acid [$R^1$=hydroxy; X=Y=F];
22. 3-(5-chlorobenzothiazol-2-ylmethyl)-3,4-dihydro-4-oxophthalazin-1-ylacetic acid [$R^1$=hydroxy; X=Cl; Y=H];
23. 3 -(5,7-dichlorobenzothiazol-2-ylmethyl)-3,4-dihydro-4-oxophthalazin- 1-ylacetic acid [$R^1$=hydroxy; X=Y=Cl];
24. 3,4-dihydro-4-oxo-3-(5-trifluoromethylbenzoxazol-2-ylmethyl)phthalazin-1-ylacetic acid [$R^1$=hydroxy; X=CF_3; Y=H];
25. 3,4-dihydro-3-(5-fluorobenzoxazol-2-ylmethyl)-4-oxophthalazin-1-yl-acetic acid [$R^1$=hydroxy; X=F; Y=H];
26. 3-(5,7-difluorobenzoxazol-2-ylmethyl)-3,4-dihydro-4-oxophthalazin-1-yl-acetic acid [$R^1$=hydroxy; X=Y=F];
27. 3-(5-chlorobenzoxazol-2-ylmethyl)-3,4-dihydro-4-oxophthalazin-1-ylacetic acid [$R^1$=hydroxy; X=Cl; Y=H];
28. 3-(5,7-dichlorobenzoxazol-2-ylmethyl)-3,4-dihydro-4-oxophthalazin-1-ylacetic acid [$R^1$=hydroxy; X=Y=Cl]; and 29. zopolrestat; 1-phthalazineacetic acid, 3,4-dihydro-4-oxo-3-[[5-(trifluoromethyl)-2-benzothiazoyl]methyl-[$R^1$=hydroxy; X=trifluoromethyl; Y=H].

In compounds 20–23 and 29, Z is S. In compounds 24–28, Z is O.

Of the above aldose reductase inhibitors, compound 4 (zenarestat) is especially preferred.

Said compounds of formula B are prepared as disclosed in U.S. Pat. No. 4,939,140.

The aldose reductase inhibitor compounds of this invention are readily available or can be easily synthesized by those skilled in the art using conventional methods of organic synthesis, particularly in view of the pertinent patent specifications.

The invention also extends to:
  the use of the said association of the ingredients i) and ii) as mentioned above in the manufacture of a medicament having anti-diabetic activity;
  the method of treating or preventing diabetes which comprises administering to a human or animal an effective dosage of the said association; and
  kits or single packages combining the active ingredients (i) and (ii) as mentioned above, useful in treating or preventing diabetes.

The ingredients i) and ii) of the association can be administered simultaneously, separately, or sequentially in any order.

Preferably, the invention extends to a method of lowering or maintaining the glucose blood level by administering to a human or animal an effective dosage of an extract, or a compound as described above, or a composition containing the same.

Preferably, the invention extends to a method of lowering or maintaining the glucose blood level by ingesting a foodstuff or beverage containing an extract, or a compound as described above.

More preferably, the invention also extends to the treatment of impaired glucose tolerance.

Still more preferably, the invention provides a protective effect, in that the glucose blood level may not substantially increase after the arrest of the administration of an extract, compound, composition and/or foodstuff or beverage described above.

A method has been described in WO 98/46243 for extracting steroidal glycosides from plant material obtained from a plant of the *Trichocaulon* or *Hoodia* genus.

The extract having anti-diabetic activity according to the invention may be prepared in accordance with the process described in WO 98/46243 for preparing an extract of a plant of the genus *Trichocaulon* or of the genus *Hoodia*, the extract comprising an appetite suppressant agent.

As described in WO 98/46243 and incorporated herein by reference, the process for preparing an extract of a plant of the genus *Trichocaulon* or of the genus *Hoodia* comprising a anti-diabetic agent includes the steps of treating collected plant material with a solvent to extract a fraction having anti-diabetic activity, separating the extraction solution from the rest of the plant material, removing the solvent from the extraction solution and recovering the extract. The extract so recovered may be further purified, e.g. by way of suitable solvent extraction procedures.

The extract may be prepared from plant material such as the stems and roots of said plants of the genus *Trichocaulon* or of the genus *Hoodia*. The genus *Trichocaulon* and the genus *Hoodia* include succulent plants growing in arid regions such as are found in Southern Africa. In one application of the invention, the anti-diabetic extract is obtained from the species *Trichocaulon piliferum*. The species *Trichocaulon officinale* may also be used to provide an active anti-diabetic extract. In another application of the invention, the active anti-diabetic extract may be obtained from the species *Hoodia currorii*, *Hoodia gordonii* or *Hoodia lugardii*.

The plant material may be homogenised in the presence of a suitable solvent, for example, a methanol/methylene chloride solvent, by means of a device such as a Waring blender. The extraction solution may then be separated from the residual plant material by an appropriate separation procedure such as, for example, filtration or centrifugation. The solvent may be removed by means of a rotary evaporator, preferably in a water bath at a temperature of 60° C. The separated crude extract may then be further extracted with methylene chloride and water before being separated into a methylene chloride extract and a water extract. The methylene chloride extract may have the solvent removed preferably by means of evaporation on a rotary evaporator and the resultant extract may be further purified by way of a methanol/hexane extraction. The methanol/hexane extraction product may then be separated to yield a methanol extract and a hexane extract. The methanol extract may be evaporated to remove the solvent in order to yield a partially purified active extract.

The partially purified active extract may be dissolved in methanol, and may be further fractionated by column chromatography, employing silica gel as an adsorption medium and a chloroform/30% methanol mixture as an eluent. A plurality of different fractions may be obtained, and each may be evaluated, by suitable bioassaying procedures, to determine the anti-diabetic activity thereof.

A fraction having anti-diabetic activity may preferably be further fractionated such as by column chromatography using silica gel as an adsorption medium and a 9:1 chloroform:methanol solvent, and the resultant sub-fractions bioassayed for their anti-diabetic activity. A sub-fraction displaying anti-diabetic activity may, if desired, be further fractionated and purified, conveniently using a column chromatographic procedure with silica gel as the adsorption medium and a 9:1 ethylacetate:hexane solvent. The resultant purified fractions may again be evaluated by suitable bioassay procedures for their anti-diabetic activity.

The Applicant has found that at least one such purified fraction has good anti-diabetic activity, and the active principle in the fraction was identified by conventional chemical techniques including nuclear magnetic resonance, and was found to be a compound of the structural formula (1) as shown above.

According to another aspect of the invention, there is provided a process for preparing an extract of a plant of the genus *Trichocaulon* or of the genus *Hoodia*, the extract comprising an anti-diabetic agent, the process including the steps of pressing collected plant material to separate sap from solid plant material and recovering the sap free of the solid plant material to form the extract.

The extract may be dried to remove moisture, e.g. by spray-drying, freeze-drying or vacuum drying, to form a free-flowing powder.

The steroidal glycosides derivatives of general formula (A) as described above having anti-diabetic activity according to the invention may be prepared as described in WO 98/46243.

The molecules chosen as the analogues or derivatives are intended to affect the properties of the steroidal trisaccharide with the aim of increasing the activity of the active ingredient. The following effects were taken into consideration when the analogues were chosen:

(i) Hydrophobic interactions and lipophilicity

Functional group modifications of the active molecule is intended to change the hydrophobicity and lipophilicity of the molecule. Increased lipophilicity has been shown to correlate with increased biological activity, poorer aqueous solubility, increased detergency/cell lysis, increased storage in tissues, more rapid metabolism and elimination, increased plasma protein binding and faster rate of onset of action.

(ii) Electronic properties and ionization constants

Functional group modification of the molecule is also intended to change the acidity and basicity which would have a major role in controlling the transport of the compound to its site of action and the binding at this target site.

(iii) Hydrogen bonding

Functional group modifications of carboxyl and carbonyl groups in the active molecule are intended to change the interactions between the proteins in biological systems and the chemically modified functional groups.

(iv) Steric parameters

The purpose of changing the steric features of the molecule is to increase binding to its receptor and thus increase its biological activity.

The following are examples of the analogues and derivatives in accordance with this invention:

a) Chemical modification of the C-12 group and ester functionality;
b) Chemical modification of the 5,6-double bond, e.g. hydrogenation and migration;
c) Chemical modification of the C-20 carbonyl and C-17 acetyl group;
d) Chemical modification of the "D" ring of the steroid or aglycone ring;
e) Modification of the carbohydrates of the trisaccharide moiety.

Accordingly, the invention provides the compounds of general formula (A), (1),(2), (3), (4), (5), (6), (7), (8), (9), (10), (11), (12), (13)(14) as shown above wherein in the general formula (A), (2), (3), (4), (5), (6), (7), (8), (9), (10), (11), (12), (13):

R=alkyl;
$R_1$=H, alkyl, tigloyl, benzoyl, or any other organic ester group;
$R_2$=H, or one or more 6-deoxy carbohydrates, or one or more 2,6-dideoxy carbohydrates, or glucose molecules, or combinations thereof,
and the broken lines indicate the optional presence of a further bond between C4–C5 or C5–C6, and/or C14–C15;
$R_3$=H, alkyl, aryl, acyl, or glucoxy.

And in the general formula (14):

R=H, alkyl, aryl or any steroid possessing a C14 beta hydroxy group, or a C12 beta hydroxy functionality, or a C17 acyl group, or a C5–C6 olefin, or combinations thereof.

The invention still further extends to a process for synthetically producing a compound having anti-diabetic activity, such as those of general formula (A), (1), (2), (3), (4), (5), (6), (7), (8), (9), (10), (11), (12), (13), (14).

The process for preparing the compounds of general formula (1), (2), (3), (4), (5), (6), (7), (8), (9), (10), (11), (12), (13), (14), their intermediates and process for preparing them are described in WO 98/46243 and are incorporated herein by reference. Compounds of formula (A) can be prepared by analogy or adaptation of this process.

The invention and its efficacy is further described, without limitation of the scope of the invention, with reference to the examples 1–41 and the drawings of the application WO 98/46243 and incorporated herein by reference, together with the following examples and drawings.

In the drawings, FIG. 1 shows a flow diagram of the general method of extracting a first crude anti-diabetic extract and a purified anti-diabetic extract from plant material of the genus *Trichocaulon* or *Hoodia;*

FIGS. 2 and 3 together show a schematic representation of a preferred embodiment of the process of the invention for producing an extract of plant material of the genus *Trichocaulon* or *Hoodia*.

EXAMPLE 1

The effects of compounds of this invention on the glucose and insulin status were assessed as follows:

Animals and Husbandry

The animals used for this study were 30 male ZDF rats and 6 male lean ZDF rats obtained from Gmi (Indianapolis, Ind., USA). The rats arrived at 6 weeks of age. The acute study was undertaken when the rats were 7 weeks old and the chronic study started when the rats were 9 weeks old.

Animals were housed under the following conditions:

| | |
|---|---|
| Temperature: | 23° C. ± 1° C. |
| Light: | 12 hours light/12 hours dark, lights on at 7 AM |

Animals were housed in plastic cages with bedding. Animals were fed a standard laboratory diet (rat and mouse breeding diet, (Beekay Feed, B & K Universal Ltd, Hull, UK)) and drinking water was provided ad libitum.

Experimental Design

Acute Study

This was a single dose, dose-response study in ZDF rats. The 30 ZDF rats were allocated to one of 5 groups so that there were 6 rats in each group. In addition there were 6 untreated lean ZDF rats. All of the rats were housed individually. The acute dose of the compound as given by oral gavage at 9.30 AM. Control ZDF and lean rats received water. Food intake was measured over the periods 9.30–16.00 (daytime) and 16.00–9.30 (night-time) for 48 hours.

Chronic Study

After a wash-out of 9 days after the acute dose, the rats were retained in the same treatment groups for the chronic study. For this study, there were two treatment groups and each treatment group had a pair-fed control group. For the pair-feeding, rats were individually matched. Pair-fed rats together with controls were dosed with water daily. Rats were dosed daily at ca 9.30 AM. The initial doses were 120 mg/kg (high dose) and 60 mg/kg (low dose).

Food and water intake were measured daily. Bodyweights were measured twice weekly. Blood samples were taken for determination of glucose, insulin and leptin. Oral glucose tolerance was also measured.

Acclimatisation

Six days prior to the single dose administration the rats were allocated to individual cages and were provided with food and water ad libitum. Four days prior to dose administration, 50 g of food was placed in each cage. Then two days prior to dose administration at ca 9.30 and 16.00 hours the food remaining was weighed and replaced with a further 50 g.

Group Allocation

Groups were assigned as follows:

| Acute Study Group | Cage | Treatment | Dose level |
|---|---|---|---|
| A | 1–6 | Water | 1 ml/kg |
| B | 6–12 | The compound (1) | 20 mg/kg |
| C | 13–18 | The compound (1) | 40 mg/kg |
| D | 19–24 | The compound (1) | 80 mg/kg |
| E | 25–30 | The compound (1) | 160 mg/kg |
| F | 31–36 | No treatment (lean litter mates) | N/A |

N/A = Not applicable

| Chronic Study Group | Cage | Treatment | Dose level |
|---|---|---|---|
| A | 1–6 | Water | 1 ml/kg |
| B | 6–12 | The compound (1) | 120 mg/kg |
| C | 13–18 | Water (pair fed group B) | 1 ml/kg |
| D | 19–24 | The compound (1) | 60 mg/kg |
| E | 25–30 | Water (pair fed group D) | 1 ml/kg |
| F | 31–36 | No treatment (lean litter mates) | N/A |

N/A = Not applicable

Groups C and D were pair fed, they received the exact amount of food (plus 1 g for waste) eaten by the respective pair rats from the treated groups in the previous 24 hours.

Test Compound Administration

Acute Study—The compound (1) was made up in water. Animals were administered with a single oral dose of The compound (1) at the appropriate rate. Control animals received water alone at the rate of 1 ml/kg. The compound (1) was administered at ca 9.30 AM. Chronic Study—The compound (1) was made up in water. Animals were dosed at the appropriate rate daily by oral gavage. Control animals received water alone at the rate of 1 ml/kg. Doses were administered at ca 10 AM each day for a total of 30 days. On Day 7 of the dosing procedure the dose levels of groups B & D were reduced to 60 mg/kg and 30 mg/kg due to concerns over that food intake suppression might be too great. The dosing procedure remained the same and animals were dosed for a further 23 days (30 days dosing in total).

Experimental Procedures

Measurement of Food and Water Intake

Daily food and water intake of each rat was measured by weight. Any spilled food was also collected and weighed so that an accurate estimate of food consumption could be made.

Measurement of Bodyweight

The bodyweight of each rat was measured twice weekly throughout the course of the study.

Blood Sampling

For measurement of blood glucose levels, a 20 µl sample of blood was taken from the tail vein whilst animals were in a fed state. A further 100 µl sample of blood was taken and the plasma separated by centrifugation (5000 rpm, 5 minutes). Plasma samples were then analysed for insulin and leptin using rat insulin or leptin ELISA kits (Crystal Chem Inc, PO Box 60225, Chicago, Ill. 60660, USA). Blood glucose, insulin and leptin levels were determined at approximately weekly intervals.

Fasted glucose, insulin and leptin levels were determined in an identical manner but animals were fasted for 5 hours prior to samples being taken.

Oral Glucose Tolerance Test (OGTT)

Oral glucose tolerance was measured at 9 days following treatment (chronic study). Animals were fasted for 5 hours prior to the start of the OGTT. Animals were treated with glucose diluted in water at a rate of 2 g/kg (1 mg/ml). Blood samples were taken at 0, 30, 60 90 and 120 minutes. Glucose concentrations were determined by mixing blood samples with 0.38 ml of haemolysis reagent. A duplicate 20 µl aliquots of this mixture was taken for each individual sample and placed in an assay tray. To each well was added 180 µl aliquots of Trinders glucose reagent. The samples were mixed and then left for approximately 30 minutes. Samples were then analysed automatically using a SpectraMax 250 and SoftMax Pro software (Molecular devices Corporation, 1311 Orleans Drive, Sunnyvale, Calif. 94089, USA). The results were converted into glucose concentration values using Prism software, version 3.0 (GraphPad Software Inc, San Diego, Calif., USA)

The OGTT was repeated after 30 days treatment. The procedure was identical except that the pair-fed rats were each given 6g of food at 7 AM with food being withdrawn at 9 AM for 5 hours.

Blood samples for insulin were obtained at 30 minutes prior to and 60 minutes post glucose load.

Regression Study

In order to determine the potential long-term effects of The compound (1), the measurement of food and water intake were continued following withdrawal of treatment.

Termination of Experiment

The experiment was terminated 36 days after the end of compound administration in the chronic study.

Statistical Analysis and Data Compilation

The significance of any differences between control animals and animals treated with The compound (1) was determined using ANOVA tests.

Results

The values reported in this section are mean values for each group of animals. Data for individual animals in are shown in the appendices.

Acute Study

Effect of The compound (1) on Food Intake

The compound (1), over the dose range 20–160 mg/kg, had no significant effect on daytime food intake over the 7 hour period post-dosing. However, it produced a dose-related reduction in the night-time food intake such that the food intake such that the food intake of ZDF rats given the 160 mg/kg dose level was the same as the lean rats.

Food intake for the period 24–48 hours past a simple oral dose was also reduced (both daytime and night-time) in a dose-related manner.

Significant reduction in food intake was only demonstrated in the first 24 hours in rats given The compound (1) (160 mg/kg) but in the second day both the effects of the 80 and 160 mg/kg doses were significant.

Chronic Study

Effect of The compound (1) on Food Intake

Daytime and night-time food intake were determined separately. Daytime intake in untreated ad-lib fed rats was approximately 25% of the night-time intake. ZDF rats ate more than the lean control rats during both day and night-time.

Treatment with The compound (1) at 120 mg/kg and 60 mg/kg produced an increasing effect on daytime intake over the first 7 days. However the full effect on night-time intake was apparent after 2 days.

As the reduction in food intake after 7 days was around 50% with both dose levels, it was decided to reduce the dosing levels to 60 mg/kg and 30 mg/kg respectively. Treatment continued for a further 21 days.

Over the period 7–14 days, there was a small reduction in the effectiveness of The compound (1) on food intake reduction but the rate of change in efficacy after reducing the dose level was slow. After 14 days food intake in both groups stabilised.

After withdrawal of the drug treatment after 28 days, food intake was monitored for a further 17 days. Surprisingly there was only a small loss of efficacy relative to the control ZDF rats.

The pattern of feeding in the pair-fed rats was not significantly different from treated animals showing the successful adoption of the pair-feeding regime.

Effect of The compound (1) on Water Intake

The ZDF rats were 9 weeks old at the start of the chronic study and their water intake relative to lean controls indicates that they were diabetic. Thus their intake was around 80 ml/rat/day as against 25 ml/rat/day for lean controls. [One control ZDF rat remained non-diabetic throughout the course of the study and all data from this rat was eliminated from the results].

Treatment with the compound (1) at either the high dose (120 or 60 mg/kg/day) or the low dose (60 or 30 mg/kg/day) reduced water intake within 4 days to the level in the lean controls and was maintained at this level throughout the dosing period. Water intake in the pair-fed groups was also reduced in an identical manner to the treated groups.

After withdrawal of the treatment after 30 days water intake of both previously treated and pair-fed controls rose slightly but even after 66 days the rats were not as diabetic as the untreated controls.

The water intake in the untreated controls rose steadily from the initial 80 ml/rat/day at the beginning of the study (rats were then 9 weeks old) to around 200 ml/rat/day after a further 4 weeks.

Effect of The compound (1) on Bodyweight

At the start of the chronic study the bodyweight of the ZDF rats was approximately 280 g whereas the lean littermates were approximately 220 g.

The bodyweight of the untreated lean littermates increased steadily throughout the course of the study to approximately 380 g at the end of the experiment. This contrasted with the control ZDF rats whose bodyweight plateaued after 3 weeks (at the age 12 weeks) at between 360–370 g. This plateau in growth rate is presumably due to the severe diabetes. Treatment with The compound (1) produced a dose-related decrease in the growth rate over the first 3 weeks of treatment relative to ZDF controls but whereas the growth rate of the ZDF controls plateaued, the growth of rats given The compound (1) continued and plateaued at a much higher level (more than 400 g). The growth rate of the pair-fed rats mirrored the effect of their corresponding treated groups. There was actual actual gain of bodyweight for the ZDF rat over the treatment period.

Effect of The compound (1) on Glucose Concentration in Fed Rats

Treatment with The compound (1) and pair feeding to the intake of ZDF rats given The compound (1) resulted in a reduction in the blood glucose concentration from the diabetic level to a similar concentration as in lean littermates after 7 days of treatment.

Normal glycaemia was maintained until withdrawal of therapy when blood glucose concentration steadily increased in a similar manner in both rats previously given The compound (1) and their pair-fed controls.

Effect of The compound (1) on Blood Glucose Concentration in Fasted Rats

Animals were fasted for 5 hours prior to taking a blood sample. Both after 8 days treatment and 29 days treatment, the blood glucose concentration of rats given The compound (1) and their pair-fed controls did not differ significantly from the concentration in lean rats and was significantly lower than that in ZDF controls.

Effect of The compound (1) on Oral Glucose Tolerance

Oral glucose tolerance was determined after 8 days and after 29 days of treatment, i.e. on day 9 and day 30. Rats were fasted for 5 hours prior to receiving an oral 2 g/kg glucose load.

The fasting blood glucose in the ZDF control rats on day 9 was around 11 mM and after the oral glucose load, rose to a mean of more than 14 mM. In contrast, rats given The compound (1) and their pair-fed controls had fasting blood glucose concentrations similar to the lean rats and glucose tolerance was only marginally impaired relative to lean. Similar results were obtained in the study conducted on day 29 except that the fasting blood glucose of the ZDF rats was higher, indicative of their advancing diabetic state.

Discussion

The inbred ($>F_{30}$ generations) Zucker diabetic male fatty rat is a recently developed model of non-insulin dependent diabetes. It is on the Zucker background and the fa gene. The original obesity trait in Zucker rats was identified by Zucker and Zucker and has since been maintained in numerous locations around the world. The original non-inbred rat model is associated with massive obesity, hyperinsulinaemia and glucose intolerance but not frank diabetes.

In contrast, the inbred ZDF/Gmi, which had its origin in a non-inbred colony in which some obese rats developed overt diabetes (1), demonstrates a characteristic and consistent diabetes (2, 3). Hyperglycaemia is initially manifest at about 7 weeks of age and all obese males are fully diabetic by 10 weeks with fed blood glucose concentrations of about 30 mM. Between 7 and 10 weeks, blood insulin concentrations fall as the pancreatic β-cells cease to respond to the glucose stimulus (4–9). The loss of response to glucose appears to be associated with the disappearance of GLUT-2 transporters on the β-cells in the islets. There is also a reduced number of GLUC-4 transporters in skeletal muscle (10–12). Thus the ZDF rat shows both an impairment of insulin action, i.e. insulin resistance and an insulin secretory defect and is recognised as a good model of non-insulin dependent diabetes. The first-line treatment for non-insulin dependent diabetes in man is diet plus exercise. Whilst the original dietary concept was a reduction in intake of carbohydrate, today it is focussed on a weight reducing diet that is low in fat, contains significant carbohydrate as polysaccharides but is low in mono and disaccharides. It should also be high in fibre. If body weight can be reduced by 5 kg then a marked improvement in diabetic control can be achieved. In practice relatively few diabetics (more than 90% of non-insulin dependent diabetic patients are overweight) are able to achieve and maintain such weight loss. Thus, there is a clear indication for therapeutic agents that will produce a reduction in obesity for the treatment of non-insulin dependent diabetes. Indeed, FDA guidelines for anti-obesity drugs specifically recognise treatment of diabetes as a secondary end-point. The compound (1) has previously been shown to reduce food intake in normal rats when administered orally. However, no previous studies have been undertaken in obese animals, which might respond differently. Furthermore, energy intake and expenditure are often closely linked and it was possible that The compound (1) might exert independent effects on intake and expenditure. Thus, as a control for possible effects unrelated to food intake, pair-fed controls were included in the current study. A further potential of the present study was to examine the possible development of pharmacological tolerance.

One previous study (13) in pre-diabetic ZDF rats has demonstrated that if 6 week old ZDF rats were diet-matched with lean littermates for 12 weeks, they remained euglycaemic. Since the rats at 6 weeks of age are pre-diabetic, then this merely demonstrates that dietary restriction will prevent the development of diabetes in this model. The present study is the first to examine the treatment of established diabetes. In order to establish dose levels for the chronic study, a single dose, dose-response study was undertaken to examine the effect on food intake. Surprisingly the effect of The compound (1) appeared to be slow in onset with little apparent effect over the first few hours. However, since the dose was administered at 09.30 and daytime food intake is only approximately 20% of the 24 h intake, it is not absolutely clear that there is a time-delay in the response, but it appears likely. Further studies in which the dose is administered just before the dark-phase are needed to clarify this point.

The duration of response to a single dose was long without effects still being seen during the second day after a single dose. As a result of the single dose study doses of 120 and 60 mg/kg/day were selected for the chronic study. The chronic administration of these dose levels produced a somewhat greater effect on food intake than was expected, possibly because of slow elimination of The compound (1). To avoid possible adverse effects of severe calorie restriction, the dose-levels were reduced after 7 days to 60 and 30 mg/kg respectively.

The compound (1) produced a marked reduction in food intake, which was sustained with no indication of tolerance. This reduction in food intake was reflected in lower initial growth rates. However, after 14 days, rats given The compound (1) had a higher growth rate than the control ZDF rats. This was because the ZDF controls had reached a plateau weight, presumably as a result of their severe diabetes. By the end of the treatment period the ZDF rats given the low dose of The compound (1) were actually heavier than the controls whilst the high dose The compound (1) rats were the same weight.

Withdrawal of the drug surprisingly did not lead to a rebound hyperphagia. Whether this indicates a long washout period for The compound (1) or it is a reflection of the difference in the diabetic status of the control ZDF rats and rats given The compound (1) is not known.

In parallel with the changes in food intake, there were substantial improvements in glycaemic status. This was reflected in direct measurements of plasma glucose and glucose tolerance as well as water intake. Since the ZDF control rats exhibit glycosuria they are profoundly polydipsic. Reduction in glycosuria results in substantial reduction in water intake. Thus the daily water intake gives an indirect measure of the level of diabetic control. It is clear that dietary restriction of ZDF rats whether direct or through the use of The compound (1) results in substantial improvement in glycaemic control.

Withdrawal of the treatment did not result in an immediate return to the diabetic state. In fact, it was approximately 2 weeks before the blood glucose concentration and water intake of rats previously given The compound (1) approached that of the diabetic controls. By which time the body weight of the previously treated rats was significantly greater than that of the ZDF controls.

The Gmi ZDF rats retain the fa/fa gene which result in point mutation in the extracellular domain in the leptin receptor conferring insensitivity to leptin. Thus the ZDF rats are obese but the obesity is curtailed by the diabetic condition. The obesity via its action on insulin sensitivity contributes to the diabetic status but the major defect in these rats that results in diabetes is pancreatic. This defect must be unrelated to the fa/fa mutation. It is clear from the above studies that The compound (1) acts on food intake independently of leptin.

Conclusion

The compound (1) is a powerful appetite suppressant in ZDF male rats and is an effective treatment in treating established diabetes.

REFERENCES

1. Clark, J. B., Palmer, C. J. & Shaw, W. N. (1983). The diabetic Zucker fatty rat. Proc. Soc. Exp. Biol. Med., 173, 68–75.
2. Peterson, Richard G. (1995). The Zucker Diabetic Fatty (ZDF) rat. In: Shafrir, E. ed. Lessons from Animal Diabetes V. Great Britain, Smith-Gordon, 225–230.
3. Peterson, R. G. (1994). Alfa Glucosidase Inhibitors: Lessons from Animal Studies. European Journal of Clinical Investigation, 24(S3), 11–18.

4. Johnson, J. H., Ogawa, A., Chen, L., Orci, L., Newgard, C. B., Alam, T. & Unger, R. H. (1990). Underexpression of b cell high $K_M$ glucose transporters in non-insulin dependent diabetes. Science, 250, 546–549.
5. Lee, Y., Hirose, H., Ohneda, M., Johnson, J. H., McGarry, J. D. & Unger, R. H. (1994). Beta-cell lipotoxicity in the pathogenesis of non-insulin dependent diabetes mellitus of obese rats: impairment in adipocyte-beta-cell relationships. Proc. Natl. Acad. Sci. USA, 91(23), 10878–10882.
6. Milburn, J. L. Jr., Ohneda, M., Johnson, J. H. & Unger, R. H. (1993). Beta-cell GLUT-2 loss and non-insulin dependent diabetes mellitus: current status of the hypothesis. (Review) Diabees Metab. Rev., 9(3), 231–236.
7. Pieber, T. R., Stein, D. T., Ogawa, A., Alam, T., Ohneda, M., McCorkle, K., Chen, L., McGarry, J. D. & Unger, R. H. (1993). Amylin-insulin relationships in insulin resistance with and without diabetic hyperglcemia. Am. J. Physiol., 265(3 Pt. 1), E446–E453.
8. Slieker, L. J., Sundell, K. L., Heath, W. F., Osborn, H. E., Bue, J., Manetta, J. & Sportsman, J. R. (1992). Glucose transporter levels in tissues of spontaneously diabetic Zucker fa/fa rat (ZDF/Drt) and viable yellow mouse ($A^{vy}/a$). Diabetes, 41, 187–193.
9. Sturis, J., Pugh, W. L., Tang, J., Ostrega, D. M., Polonsky, J. S. & Polonsky, K. S. (1994). Alterations in pulsitile insulin secretion in the Zucker diabetic fatty rat. Am. J. Physiol., 267 Endocrinol. Metab., 30, E250–259.
10. Dohm, G. L., Friedman, J. E. & Peterson, R. G. (1993). Acarbose treatment of non-insulin dependent diabetic fatty (ZDF/Drt-fa) rats restores expression of skeletal muscle glucose transporter GLUT-4. In: Drugs in Development, Volume 1, a-Glucosidase Inhibition: Potential Use in Diabetes. Vasselli, J. R., Maggio, C. A. & Scirabine, A., eds., Branford, Conn.: Neva Press, 173–180.
11. Dolan, P. L., Tapscott, E. B., Peterson, R. G. & Dohm, L. D. Differential effects of acarbose feeding on glucose transport and GLUT-4 protein in lean and obese diabetic ZDF rats. Submitted for publication.
12. Friedman, J. E., De Vente, J. E., Peterson, R. G. & Dohm, G. L. (1991). Altered expression of muscle glucose transporter GLUT-4 in diabetic fatty Zucker rats (ZDF/Drt-fa). Am. J. Physiol., 261 (Endocrinol. Metab. 24), E782–788.
13. Ohneda, M., Inman, L. R. & Unger, R. H. (1995). Caloric restriction in obese pre-diabetic rats prevents beta-cell depletion, loss of beta-cell GLUT-2 and glucose incompetence. Diabetologia, 38(2), 173–179.

EXAMPLE 2

Harvested *Hoodia* plants received either from the natural environment or through a cultivation programme are first stored at 4° C. for a maximum of 48 hours. The plants are washed in tap water and thereafter sliced into ±1 cm slices. The sliced pieces are all combined and then pressed through a hydraulic press at 300 bar pressure for a minimum of 0.5 hour per pressing. During the pressing the sap of the plant is collected separately. The sap is stored at −18° C. until further processing is required.

The sap is spray-dried under suitable conditions to obtain a free flowing powder. The moisture content in the powder is preferably less than 5% after spray drying and, if necessary, it is further dried in a vacuum oven or using a fluid bed drier.

Both the sap and the spray-dried material have been shown effective as an anti-diabetic in biological assays in rats.

Experimental 50 kg of *Hoodia gordonii* plants were washed with tap water and thereafter sliced into 1 cm slices. The sliced plants were then pressed through a hydraulic press at 300 bar for a minimum of 0.5 hour per batch. The sap was collected and the mass was found to be 10 kg when *Hoodia gordonii* plants from the environment were used, and 20 kg when *Hoodia gordonii* plants from the cultivation programme was used. The sap (500 g) was spray-dried using the following conditions:

| Flow rate | 2.85 ml/min |
|---|---|
| Inlet temperature | 110° C. |
| Outlet temperature | 70° C. |
| Chamber temperature | 78° C. |

The spray-dried powder obtained was a free flowing powder (22 g) with a moisture content of 6.9%.

The spray dried powder was analysed for active ingredient concentration using HPLC techniques. The concentration of the active was determined to be 13 g/kg of spray dried powder.

HPLC Analysis Method

| Eluant | Acetonitrile: water (7:3), isocratic |
|---|---|
| Column | Reverse phase C-18 |
| UV absorbance | 225 nm |
| Flow rate | 1 ml/min |
| Injection volume | 10 μl |

Method

Spray-dried powder (10 mg) was dissolved in water (0.5 ml) and acetonitrile (0.5 ml) 10 μl of this solution was injected into the HPLC and the concentration of the active compound (1) was determined using a standard curve as a reference which had been prepared from the pure compound (1).

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The invention claimed is:

1. A method of treating Type II diabetes by administering to a human or other mammal in need thereof an effective dosage of an extract of a plant of the genus *Trichocaulon* or of the genus *Hoodia*, wherein the extract comprises the compound of formula (1):

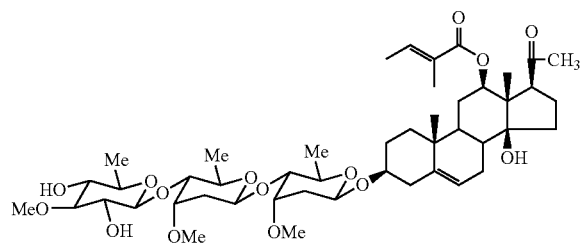

2. The method according to claim 1, wherein said plant of the genus *Trichocaulon* is selected from the group consisting of *Trichocaulon piliferum* and *Trichocaulon officinale* and said plant of the genus *Hoodia* is selected from the group consisting of *Hoodia currorii, Hoodia gordonii* and *Hoodia lugardii*.

3. The method according to claim 1, wherein the extract is obtained by a process comprising the steps of treating collected plant material with a solvent to isolate a solution of an extract having anti-diabetic activity, separating the solution of the extract from the rest of the plant material, removing solvent from said solution and recovering said extract.

4. The method according to claim 3, wherein the process further comprises the step of concentrating the anti-diabetic activity of said extract by further extraction with a solvent.

5. The method according to claim 3, wherein said solvent of said solvent treatment extraction step or steps is one or more of methylene chloride, water, methanol, hexane, ethyl acetate or mixtures thereof.

6. The method according to claim 3, wherein the process further comprises the step of concentrating the anti-diabetic activity of said extract by chromatographic separation.

7. The method according to claim 6, wherein said chromatographic separation employs one or more of chloroform, methanol, ethyl acetate, hexane or mixtures thereof as an eluant.

8. The method according to claim 6, wherein the process includes carrying out the chromatographic separation on a column, collecting an eluate in fractions from the column, evaluating the fractions to determine their anti-diabetic activity, and selecting at least one fraction containing anti-diabetic activity.

9. The method according to claim 1, wherein said extract is obtained by a process comprising steps of pressing collected plant material to separate sap from solid plant material and recovering the sap free of the solid plant material to form the extract.

10. The method according to claim 1, wherein said extract is processed to form a free-flowing powder.

11. The method according to claim 1, wherein said extract is administered in a foodstuff or beverage to have an anti-diabetic effect when ingested.

12. A method for treating or preventing Type II diabetes comprising the step of administering to a human or other mammal in need thereof an effective dosage of a composition comprising the extract according to claim 1.

13. The method according to claim 12, wherein said composition is administered in a dosage amount of from 0.05 mg/kg/day to 100 mg/kg/day.

14. The method according to claim 13, wherein the dosage amount is 0.1 mg/kg/day to 50 mg/kg/day.

15. A method of treating diabetes comprising the step of administering to a human or other mammal in need thereof an effective dosage of the following ingredients
i) an extract of a plant of the genus *Trichocaulon* or of the genus *Hoodia* in association with
ii) one or more other agents selected from the group consisting of anti-diabetics, glycogen phosphorylase inhibitors, sorbitol dehydrogenase inhibitors, glucosidase inhibitors and aldose reductase inhibitors,
wherein the extract comprises the compound of formula (1):

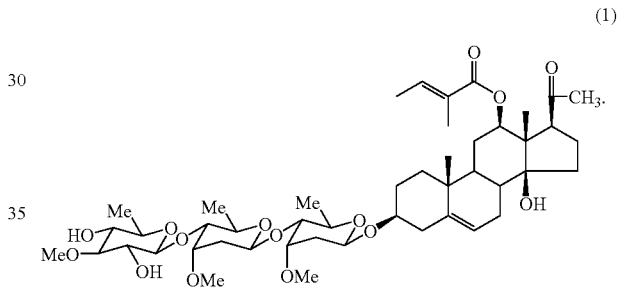

(1)

16. The method according to claim 15, wherein the ingredients i) and ii) are simultaneously, separately, or sequentially administered.

17. The method according to claim 1, wherein said plant of the genus *Hoodia* is *Hoodia currorii*.

18. The method according to claim 1, wherein said plant of the genus *Hoodia* is *Hoodia gordonii*.

19. The method according to claim 1, wherein said plant of the genus *Hoodia* is *Hoodia lugardii*.

* * * * *